(12) United States Patent
Allaway

(10) Patent No.: US 11,096,762 B2
(45) Date of Patent: *Aug. 24, 2021

(54) METHOD, SYSTEM, AND DEVICE FOR PLANNING AND PERFORMING GUIDED AND FREE-HANDED TRANSPERINEAL PROSTATE BIOPSIES

(71) Applicant: Corbin Clinical Resources, LLC, Cumberland, MD (US)

(72) Inventor: Matthew J. Allaway, Cumberland, MD (US)

(73) Assignee: Corbin Clinical Resources, LLC, Cumberland, MD (US)

( * ) Notice: Subject to any disclaimer, the term of this patent is extended or adjusted under 35 U.S.C. 154(b) by 519 days.

This patent is subject to a terminal disclaimer.

(21) Appl. No.: 16/115,180

(22) Filed: Aug. 28, 2018

(65) Prior Publication Data

US 2018/0360557 A1    Dec. 20, 2018

Related U.S. Application Data

(63) Continuation of application No. 14/677,286, filed on Apr. 2, 2015, now Pat. No. 10,064,681.
(Continued)

(51) Int. Cl.
*A61B 90/00*    (2016.01)
*A61B 8/08*    (2006.01)
(Continued)

(52) U.S. Cl.
CPC ............ *A61B 90/39* (2016.02); *A61B 8/0841* (2013.01); *A61B 8/12* (2013.01); *A61B 10/0241* (2013.01);
(Continued)

(58) Field of Classification Search
CPC ......... A61B 90/39; A61B 8/0841; A61B 8/12; A61B 10/0241; A61B 10/04;
(Continued)

(56) References Cited

U.S. PATENT DOCUMENTS 4,776,346 A    10/1988 Beraha
4,911,173 A    3/1990 Terwilliger
(Continued)

OTHER PUBLICATIONS

Australian Examination Report No. 1, AU 2015240520, dated Dec. 17, 2018.
(Continued)

*Primary Examiner* — Sanjay Cattungal
(74) *Attorney, Agent, or Firm* — Polsinelli PC

(57) ABSTRACT

A system for planning and performing a guided and free-handed transperineal prostate biopsy includes a transrectal ultrasound probe, an access needle configured to perforate a perineal access site of a patient, a biopsy gun, and a guide. The guide includes a sliding platform, stabilization bars, upper and lower mounts, and fasteners. The system and guide apparatus is used for locating a target area using the ultrasound probe, positioning the ultrasound and the access needle at respective designated points, precisely measuring the distance to a designated point, and obtaining specimens from a precise point in the prostate, wherein the method is performed free-handed, and multiple tissue or cell specimens may be obtained from the prostate through an initial access needle.

43 Claims, 12 Drawing Sheets

Related U.S. Application Data

(60) Provisional application No. 61/974,826, filed on Apr. 3, 2014.

(51) Int. Cl.

| | | |
|---|---|---|
| *A61B 8/12* | (2006.01) | |
| *A61B 10/02* | (2006.01) | |
| *A61B 10/04* | (2006.01) | |
| *A61B 17/34* | (2006.01) | |
| A61B 17/00 | (2006.01) | |
| A61B 18/00 | (2006.01) | |
| A61B 18/02 | (2006.01) | |
| A61B 18/12 | (2006.01) | |

(52) U.S. Cl.
CPC .......... *A61B 10/04* (2013.01); *A61B 17/3403* (2013.01); *A61B 18/02* (2013.01); *A61B 18/12* (2013.01); *A61B 2010/045* (2013.01); *A61B 2017/00274* (2013.01); *A61B 2017/00477* (2013.01); *A61B 2017/3413* (2013.01); *A61B 2018/00547* (2013.01)

(58) Field of Classification Search
CPC ..... A61B 17/3403; A61B 18/02; A61B 18/12; A61B 2017/00274; A61B 2018/00547; A61B 2017/00477; A61B 2010/045; A61B 2017/3413

See application file for complete search history.

(56) References Cited

U.S. PATENT DOCUMENTS

| | | | |
|---|---|---|---|
| 5,047,036 A | 9/1991 | Koutrouvelis | |
| 5,494,039 A * | 2/1996 | Onik | A61B 17/3403 |
| | | | 600/461 |
| 5,800,389 A | 9/1998 | Burney | |
| 6,485,469 B1 | 11/2002 | Stewart et al. | |
| 10,743,910 B2 | 8/2020 | Allaway | |
| 10,743,911 B2 | 8/2020 | Allaway | |
| 2002/0061300 A1 | 5/2002 | Gokcen | |
| 2002/0087152 A1 | 7/2002 | Mikus et al. | |
| 2002/0123689 A1 | 9/2002 | Furia | |
| 2003/0153850 A1* | 8/2003 | Davis | A61B 8/4209 |
| | | | 601/2 |
| 2003/0212414 A1 | 11/2003 | Sonek | |
| 2004/0162458 A1* | 8/2004 | Green | A61N 5/1007 |
| | | | 600/7 |
| 2004/0167542 A1 | 8/2004 | Solar | |
| 2005/0159676 A1* | 7/2005 | Taylor | A61B 10/0275 |
| | | | 600/567 |
| 2005/0283120 A1 | 12/2005 | Wang | |
| 2006/0241477 A1 | 10/2006 | Sasady | |
| 2007/0043291 A1* | 2/2007 | Fidel | A61N 5/1048 |
| | | | 600/439 |
| 2007/0073219 A1 | 3/2007 | Yang | |
| 2007/0233157 A1 | 10/2007 | Mark | |
| 2008/0004481 A1* | 1/2008 | Bax | A61N 5/1001 |
| | | | 600/7 |
| 2008/0154198 A1 | 6/2008 | Wei | |
| 2009/0030339 A1* | 1/2009 | Cheng | A61B 8/0841 |
| | | | 600/562 |
| 2009/0093715 A1 | 4/2009 | Downey | |
| 2009/0292224 A1 | 11/2009 | Bowman | |
| 2010/0036245 A1 | 2/2010 | Yu et al. | |
| 2011/0071380 A1* | 3/2011 | Goldenberg | A61B 8/0841 |
| | | | 600/411 |
| 2011/0319759 A1* | 12/2011 | Liu | A61B 10/0241 |
| | | | 600/439 |
| 2012/0245455 A1* | 9/2012 | Bauman | A61B 17/3403 |
| | | | 600/424 |
| 2014/0039314 A1* | 2/2014 | Stoianovici | A61B 34/30 |
| | | | 600/439 |
| 2014/0094774 A1 | 4/2014 | Blanchard | |
| 2015/0119715 A1* | 4/2015 | Baumann | A61B 8/0841 |
| | | | 600/444 |
| 2015/0366544 A1* | 12/2015 | Yap | A61B 8/4209 |
| | | | 600/464 |

OTHER PUBLICATIONS

European Examination Report, EP 15773805.5, dated Sep. 2, 2019.
Final Office Action, U.S. Appl. No. 14/874,104, dated Jan. 17, 2020.
Non-Final Office Action, U.S. Appl. No. 14/874,104, dated Jul. 23, 2019.
Non-Final Office Action, U.S. Appl. No. 16/377,597, dated Jan. 22, 2020.
Non-Final Office Action, U.S. Appl. No. 16/377,597, dated Sep. 26, 2019.
Non-Final Office Action, U.S. Appl. No. 16/377,754, dated Jan. 17, 2020.
Non-Final Office Action, U.S. Appl. No. 16/377,754, dated Sep. 26, 2019.
Response to Final Office Action, U.S. Appl. No. 14/874,104, dated Apr. 16, 2020.
Response to Non-Final Office Action, U.S. Appl. No. 14/874,104, dated Oct. 21, 2019.
Response to Non-Final Office Action, U.S. Appl. No. 16/377,597, dated Dec. 19, 2019.
Response to Non-Final Office Action, U.S. Appl. No. 16/377,597, dated Apr. 22, 2020.
Response to Non-Final Office Action, U.S. Appl. No. 16/377,754, dated Dec. 13, 2019.
Response to Non-Final Office Action, U.S. Appl. No. 16/377,754, dated Apr. 16, 2020.
Response to Restriction Requirement, U.S. Appl. No. 14/874,104, dated Mar. 20, 2019.
Restriction Requirement, U.S. Appl. No. 14/874,104, dated Jan. 22, 2019.
Extended European Search Report, EP21153023.3, dated May 3, 2021.

* cited by examiner

METHOD, SYSTEM, AND DEVICE FOR PLANNING AND PERFORMING GUIDED AND FREE-HANDED TRANSPERINEAL PROSTATE BIOPSIES

CROSS-REFERENCE TO RELATED APPLICATIONS

This application is a continuation application of U.S. application Ser. No. 14/677,286 filed Apr. 2, 2015, which application claims the benefit of U.S. Provisional Patent Application No. 61/974,826, titled "METHOD, SYSTEM, AND DEVICE FOR PLANNING AND PERFORMING GUIDED AND FREE-HANDED TRANSPERINEAL PROSTATE BIOPSIES", filed Apr. 3, 2014. The entire disclosure of each application referenced above is hereby incorporated by reference herein.

FIELD

The disclosure relates to biopsy procedures and systems. In particular, the disclosure relates to methods, systems, and apparatus useful for planning and performing guided and free-handed transperineal prostate biopsies.

BACKGROUND

A biopsy is a medical procedure that involves sampling and removing tissues or cells from a living body for further examination and analysis. A prostate biopsy may be performed by a care provider for diagnosis and treatment of a patient's prostate. For example, the vast majority of patients with an abnormal prostate specific antigen (PSA) or suspicious results from a digital rectal examination (DRE) undergo biopsy. Typical biopsy procedures include transrectal ultrasound-guided (TRUS) biopsies and transperineal ultrasound-guided (TPUS) biopsies.

TRUS involves obtaining tissue or cell specimens by passing a biopsy needle or other biopsy instruments through the rectal wall and into the prostate at various locations using a sagittal imaging plane. The biopsy needle or other biopsy instruments may be guided by ultrasound in a sagittal plane. There are disadvantages associated with TRUS. In particular, the patient may be required to take antibiotics prior to the procedure to reduce the risk of infections. Also, TRUS requires the patient to perform bowel preparation, which is a procedure usually undertaken before the biopsy, for cleansing the intestines of fecal matter and secretions. Further, the passage of the biopsy needle through the rectal wall may introduce bacteria from the rectum into the prostate, such as coliform bacteria that may lead to an infection or other complications. Additionally, many clinically significant prostate cancers are found in locations of the prostate that are often too difficult to access when using the transrectal approach.

TPUS includes obtaining tissue or cells specimens by passing one or more biopsy needles through the perineum and into the prostate. TRUS has been favored over TPUS. Unlike TRUS, TPUS does not require a patient to take antibiotics prior to the procedure or to undergo the bowel preparation for lowering the risk of bacterial issues. Further, TPUS uses a more effective route to access the prostate and is capable of accessing target locations that may be difficult to access utilizing the transrectal approach in comparison with TRUS. In addition, the needle does not pass through the rectal wall which eliminates the risk associated with TRUS of coliform bacteria entering the prostate or the bloodstream.

Systems configured for TPUS include a biopsy grid that may be fixed to, for example, a floor, platform, or table on which the patient receiving the biopsy lies. The biopsy grid may provide multiple apertures through which a biopsy needle or other biopsy instruments may be inserted. An ultrasound probe is fixed directly to the apparatus and is used to axially guide the biopsy needle or other instruments, for example other biopsy instruments. Thus, TPUS systems require imaging in an axial plane of the ultrasound or a transverse transducer for positioning the biopsy needle.

SOME EXAMPLE EMBODIMENTS

Related art systems and prostate biopsy TPUS methods do not allow free-hand movement of the ultrasound probe, and heavily rely on the axial ultrasound plane to confirm positioning of the biopsy needle or other instruments. Moreover, such systems and methods include extracting prostate tissue specimens by delivering separate punctures into the transperineal tissue. Also, a care provider executing TPUS procedure using related art systems may experience substantial difficulty in freely handling and positioning a biopsy needle at a desired target location of the prostate relying on the sagittal plane in using the TRUS methods.

An apparatus in accordance with an embodiment may include an upper mount and a lower mount. The lower mount may be configured to connect with the upper mount to secure a transrectal probe therebetween. The upper mount may be configured to support an access needle, the access needle configured for perforation of subcutaneous tissue of a perineum at an access site of a target area of a patient. The upper mount may be configured to guide the access needle whereby movement of the access needle is fixed relative to movement of the transrectal probe.

A system in accordance with an embodiment may include a biopsy guide and a transrectal transducer fixed to the biopsy guide. The biopsy guide may be configured to guide an access needle to perforate an access site in subcutaneous tissue of a perineum, whereby movement of the access needle is fixed relative to a movement of the transrectal transducer.

A method of performing a prostate biopsy in accordance with an embodiment may include imaging a prostate in an axial plane and a sagittal plane with a transducer providing a real-time image, locating a target area of the prostate, and positioning an access needle and an access site in subcutaneous tissue of a perineum wherein the access site is at a midpoint between a lateral edge of the prostate and a urethra along a first axis and a midpoint between an anterior capsule and a posterior capsule along a second axis. The method may include guiding a biopsy instrument along a sagittal plane to the target using the real-time image, and obtaining one or more specimens of the prostate through the access needle with a biopsy instrument.

Accordingly, there is a demand for transperineal biopsy methods, systems, and apparatus that enables a biopsy that is less burdensome for the patient and for the practitioner performing the biopsy, increased guidance of needle or other biopsy instruments, and with a higher rate of efficacy and lower rate of health risk than related art TPUS and TRUS systems and methods. Apparatus, systems, and methods disclosed herein satisfy these demands.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF SOME EMBODIMENTS

Figure 1:
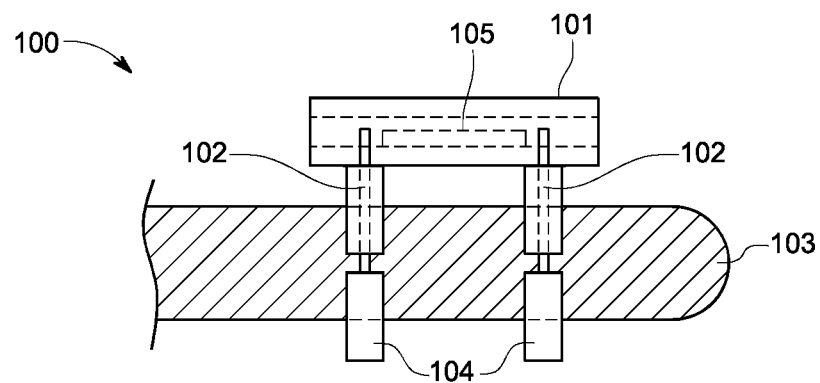
FIG. 1 shows a side view of a guide secured to a probe in accordance with an embodiment.

The apparatus, systems, and methods provided herein enable real-time visualization, free-handed, guided, and multi-sample transperineal methods for performing a biopsy. The methods, systems, and apparatus provided herein also enable a complete biopsy of the prostate with only one perforation, or with minimal perforations of a patient's skin by way of an initial access site, such that the access needle is freely moveable. The biopsy guide may be placed on or fitted to an assortment of ultrasound probes of different sizes and shapes due to an adjustable mounting system. The guide may be configured to fit to the probe using any suitably configured fastening system. For example, the guide may be configured as a sleeve that is formed to slide over an end of a probe and into an operable position. Alternatively, the guide may be configured to fit to a probe using screws, flanges, zip ties, or other temporary, permanent, or semi-permanent fastening systems.

In one embodiment, the guide allows biopsies of one or more tissue or cell samples to be obtained through an initial access needle, while providing direct, real-time ultrasound visualization by, for instance, fixing a position of the access needle relative to an ultrasound probe to provide. For example, the guide is fixed to an ultrasound probe that is not fixed and may be freely moveable in operation. Stabilization bars that are built into the guide facilitate the positioning and holding of the perineal skin and subcutaneous tissue to allow positioning of the access needle. The position of the access needle is facilitated by locking the access needle into the subcutaneous tissue of the perineum using a sliding platform that allows a user, such as a medical practitioner or patient caregiver, to place the access needle along a sagittal transducer plane at optimal positions for obtaining prostate biopsies. In some embodiments, upon placement of the access needle into a locked position, for example, in the pelvic floor, a user may then pass a biopsy needle through the access needle to a desired location of the prostate. In yet further embodiments, the passing of the biopsy needle through the access needle and to the prostate may be facilitated by direct sagittal plane visualization based on the alignment of the access needle.

Methods and systems provided herein do not require a patient to take antibiotics at any point prior to the biopsy procedure, nor do they require a patient to undergo bowel preparation in advance of the procedure. Methods, systems, and apparatus can reduce or eliminate multiple skin perforations by using a single access location or access site, while allowing multiple extractions of tissue or cell specimens from the prostate. Methods, systems, and apparatus in accordance with embodiments allow for real-time visualization during a free-handed, guided, transperineal approach, while also facilitating a complete assessment of the prostate with, for example, only one perforation of the patient's skin wherein the access needle is freely moveable in each plane.

Methods, systems, and apparatus of embodiments may include and facilitate treatment that uses a cryoablation probe for focal therapy of prostate cancer, a radiofrequency instrument, a thermotherapy instrument, any instrument for treatment of the cancerous area, or a combination of any of these instruments.

Methods, systems, and apparatus of embodiments enable planning and performing the free-hand transperineal prostate biopsies under the guidance of a device and of a real-time transducer in the sagittal imaging plane.

The biopsy is performed using a system that includes a biopsy guide, a transducer, an access needle, and a biopsy instrument. The access needle may allow the anesthesia to be injected into the patient, and the tissue or cell specimens of the prostate to be extracted. If anesthesia is used, a syringe may be included in the system. The transducer may be an ultrasound probe or any other type of device that is capable of causing a visualization of the prostate in a display device. In embodiments, the biopsy guide may be disposable. In embodiments, the biopsy guide may be formed of materials intended for a single use. In other embodiments, the biopsy guide is reusable. In some embodiments, the biopsy guide may be formed of materials intended for multiple uses.

The guide may include a sliding platform, stabilization bars, one or more upper and lower mounts, and a fastener. The upper and lower mounts may be curvilinear in shape. The upper and lower mounts may be positioned proximally or distally along an ultrasound probe, such as a transrectal ultrasound probe. The configuration and positioning of the upper and lower mounts are adjustable based on the shape of the ultrasound probe and the patient's body habitus.

The guide may be made of any material such as a plastic or metallic material. The guide may be disposable and made of a biodegradable plastic material. In other embodiments, the guide may be reusable and made of stainless steel. The dimensions, for example, the length, width, height, depth, and breadth of the sliding platform, stabilization bars, upper and lower mounts, and the fastener may vary and may be adjustable. The variable and adjustable dimensions, for example, of the stabilization bars, provide a user with flexibility in achieving and maintaining the guide in an appropriate ultrasound plane while performing biopsy procedures, while the user's patients may vary in size and levels of perineal subcutaneous tissue and fat. In a patient with an excessive amount of perineal subcutaneous tissue and fat, a larger stabilization bar will assist in locking the guide in the proper ultrasound plane.

The adjustable stabilization bars and mounts may be curvilinear in shape, allowing the guide to be placed proximally or distally along any cylindrical instrument, such as the transrectal ultrasound probe, which is determined by the surgeon based on the shape of the probe and the patient's body habitus. This allows the guide to be mounted to any assortment of ultrasound probes. Similarly, the platform may, for example, have various thicknesses.

The stabilization bars may be fixed to a top portion of the upper curvilinear mounts of the guide, and may extend beyond the front edge of the upper mounts. The stabilization bars may extend beyond the front edge of the upper curvilinear mount by approximately 8 mm. The guide may be approximately 60 mm wide, or the guide may be approximately 50 mm long, for example. The stabilization bars may have grooves for accommodating a sliding platform that is shorter in length than the stabilization bars. The grooves being configured to allow the platform to slide forward and backward along the stabilization bars.

An inner portion of the stabilization bars may have built-in grooves. The grooves accommodate a sliding platform which is shorter in length than the stabilization bars. This allows the sliding platform to slide from the back to the front of the stabilization bars. The stabilization bars may include a resistance as to prevent the sliding bar to freely move back and forth on the stabilization bar. This resistance may be introduced by the sliding platform or both the stabilization bar and the sliding platform. The resistance may be provided by a strip of rubber or any other material capable of providing friction or other. The strip may be curvilinear. The resistance may be generated by a mechanical system, such as a spring mechanism.

The sliding platform may have a hole through the platform. In some embodiments, the hole is drilled in the center of the platform. The hole can accommodate various types of needles, including access needles having various diameters, for example, spinal needles having a gauge in the range of 14-18. The hole can also accommodate needles having various lengths. The lengths of the needle may depend, in part, on the body habitus. The needle may be a reusable needle, such as a reusable spinal needle. The needle may be a disposable needle, such as a disposable spinal needle.

A flange of the guide secures the placement of the access needle to the guide. The flange may be configured to snap into the guide to secure the needle. The flange may be secured to the guide by other securing mechanisms. The flange can be of various shapes and configurations. For example, the flange may be u-shaped. As another example, the flange may have a thin or slim configuration. The guide assists in providing the appropriate angle of penetration and direction of the access needle, or other instruments that may be used in combination with the guide.

The hole in the guide is placed so that once the guide is mounted to the ultrasound probe, the drilled hole will be parallel to the sagittal transducer. The drilled hole may also accommodate the tip of a biopsy gun, or any other biopsy instrument. The sliding platform may be interchangeable and may be removed to allow placement of another sliding platform with a different sized to permit different sizes of needles and other instruments. The hole may be configured to accommodate a cryoablation instrument, a radiofrequency instrument, thermotherapy instrument, or any other instrument for diagnosis and treatment of a bodily tissue, including a cancerous area of a prostate.

The platform may have or define a predrilled hole in the center of the platform that can accommodate various sizes of needles and instruments. For example, the hole may be configured to accommodate a needle having a range of 14-18 gauges, such as a reusable 14 gauge spinal needle. Central hole placement on the platform provides enables alignment of the hole with a sagittal transducer when the guide is mounted to an ultrasound probe. The platform may have multiple holes to accommodate various applications and body habitus. Further, the platform may be of various thicknesses.

Once the one or more upper curvilinear mounts are placed at the desired location on the transrectal ultrasound probe, the access hole for a needle, such as a 14 gauge reusable spinal needle, will remain a fixed distance from the ultrasound probe. In embodiments, having one or more lower curvilinear mounts, the mounts may be positioned to cradle an upper aspect of the ultrasound probe.

At least two lower mounts are provided and may be individually positioned to accommodate various types of probes, which may have variable diameters along their shafts. In embodiments, a probe, such as a transrectal ultrasound probe, may have one or more diameters along the probe's shaft. In yet further embodiments, one end of the guide may be fixed at a location of the probe having a different diameter than the location where the other end of the guide is fixed. The separate lower mounts allow for the fixation of the guide, even with varying probe diameters.

The lower mount of the guide may include a lower right mount and a lower left mount connected by an adjustable mid joint or fastener. The adjustable mid joint or fastener allows the guide to be secured to the probe even if the diameter of the shaft of the probe is longer than the width of the lower mount. The mid joint or fastener may be flexible to allow the right lower mount to form an acute angle with the left lower mount. This also allows for fixation of the guide to a probe shaft that is not circular in shape.

The lateral edges on both ends of the lower mounts may contain a notched post. Corresponding locations of the upper mounts contain holes, such as square shaped holes, to accommodate the notched post of a corresponding lower mount. An upper aspect of each hole includes a flange for locking the notched post in a fixed position. This configuration allows the lower mounts and the upper mounts to be secured to each other and to the probe.

Methods may include locating a suspicious area, positioning an access needle, and obtaining one or more tissue or cell specimens from an accurate point in the prostate. The method allows for multiple tissue or cell specimens to be obtained from a bodily organ, such as the prostate, and permits access to the prostate from different angles through a single initial access needle. The method may include calculating the volume of the prostate by positioning the access needle at a mid point in the x axis from the lateral edge of the prostate to the urethra.

Methods may be performed using no anesthesia. Alternatively, an anesthetic may be used. For example, the anesthetic may be lidocaine, or any type of local anesthetic. The lidocaine may include 1 or 2% of a lidocaine solution.

The suspicious area or bodily organ may be located by using a transducer. The transducer may be any type of probe for accessing and viewing a targeted site or object, such as an ultrasound probe, or any type of transducer capable of providing visualization of the prostate and/or instruments and devices for diagnosis and treatment of the tissue. The biopsy may be performed using a biopsy gun, a suction device, or any type of instrument that is small enough to be introduced through the access needle and capable of extracting the tissue or cell specimen. The biopsy may be performed while the patient is in a dorsal lobothy position, prone position, or any position that allows for access to the perineal area.

Methods may include applying an antiseptic solution to the perineal area. The antiseptic solution may include betadine, or any other substance that reduces the possibility of infection, sepsis, or putrefaction. Methods may include applying bacitracin to the skin at the puncture site or any other type of topical preparation for preventing the possibility of infection.

Methods may include attaching a needle to a luer lock syringe, which may contain an anesthetic, or any other type of device capable of retaining its contents and dispensing its contents through the needle. A biopsy gun or any other instrument that may be attached to the needle and used for inserting or extracting any substance thru the lumen of the access needle.

Methods may include releasing the syringe from the needle after the anesthetic is injected. Methods may include dividing the prostate in three different regions and designating lateral, mid, apical prostate, and may include labeling the tissue or cell specimen containers, which will identify the tissue or cell specimens.

Methods may include securing the guide to the probe. This will permit the practitioner to take the biopsy gun as many times as necessary using his/her other hand, and, consequently, extract multiple tissue or cell specimens. It is contemplated that this can be done without assistance of any other person, and that the biopsy gun may also be attached to the guide in order to permit the surgeon to, for example, label the container with the tissue or cell specimen while performing the biopsy. Methods may also include monitoring all the actions in the prostate by way of a display device that provides images captured by the probe.

Methods may include moving the needle in x, y, and z planes. By being able to move the needle in x, y, and z planes, the surgeon is capable of extracting tissue or cell specimens from several different areas of the prostate without having to retrieve the needle and preventing other perforation of the patient's skin. In embodiments, movement of the needle within the patient's body is facilitated by using a display device.

Methods may include removing the access needle from the perineal area. This may be done while the biopsy gun is secured to the access needle or after the biopsy gun has been detached from the access needle.

Methods may include realigning the needle in the desired prostate region. If the surgeon wishes to start at the right lateral prostate region and notices that the needle tip is not directed at the lateral region, the surgeon rolls the ultrasound probe slightly and to note that the needle tip is directed to the desired region, then the surgeon may realign the needle to obtain tissue or cell specimen. The surgeon may realign the needle using one hand while having the needle attached to the biopsy gun, which may be attached to the probe through the guide.

Methods may include identifying the areas in which biopsy have already been performed. After each extraction of tissue or cell specimen during the biopsy, a hyperechoic streak remains visible on ultrasound display. This allows the surgeon to identify the area of the prostate and that an extraction has been made, as to allow the surgeon to prevent overlap of extractions.

In another embodiment, the method includes identifying the path of the urethra. This allows the surgeon from preventing passing the biopsy needle thru or into this path.

FIG. 1 is a side view of a guide 100 secured to a probe including a stabilization bar 101, fasteners 102, probe 103, lower mounts 104, and an upper mount 105. The stabilization bar 101 is an extension of the upper mount 105, as further discussed in FIG. 4. In embodiments, the distance between the fasteners 102 and the upper mount 105 may be adjustable to accommodate various applications and body habitus.

Figure 2A:
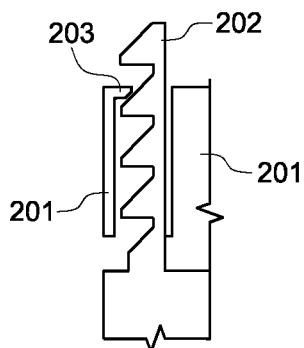
FIG. 2A shows an internal view of a guide fastener in accordance with an embodiment.

FIG. 2A is an internal view of a guide's fastener, including an aperture 201, teeth 202, and a flange 203. The flange 203 may be an extension of the aperture 201, which is part of the upper mount 105. Aperture 201 will allow the teeth 202 to be inserted into the upper mount 105, and the flange 203 will lock the teeth 202, which is connected to lower mount 104, to the upper mount 105. The aperture 201 with flange 203 and teeth 202 allows for adjusting the height of the guide 100.

In one embodiment, the fastener (e.g., via the aperture 201, flange 203, and/or the teeth 202) can be configured to fasten the guide 100 to the probe 103 with, e.g., varying levels of tension to provide for adjustments of the relative positions of the guide 100 and the probe 103 even after the guide 100 has been mounted to the probe 103. For example, the fastener 102 can provide a first level of tension sufficient to hold the position of an access needle (e.g., introduced through a hole or other needle mount of the guide 100) rotationally fixed to the probe 103 while still allowing for a forward or reverse sliding of the probe 103 with respect to the guide 100. By way of example, the forward or reverse sliding adjustment can be performed to adjust the penetration depth of the probe 103 with respect to the patient depending on a size of the patient. Once the final adjustment is made, the fastener can be actuated to final position or tension that will then lock further adjustments of the positioning of the guide 101 relative to the probe 103.

It is noted that the guide's fastener as described above is one example embodiment among other possible example fasteners that are applicable to various embodiments of the guide 100. Accordingly, it is contemplated that various embodiments of the guide 100 may use any now known or later developed fastening system that can secure the guide 100 to the probe 103.

Figure 2B:
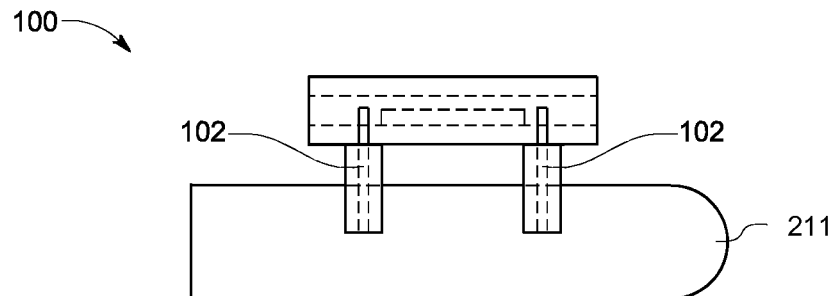
FIG. 2B shows a sheath-based guide fastener in accordance with an embodiment.
Figure 2C:
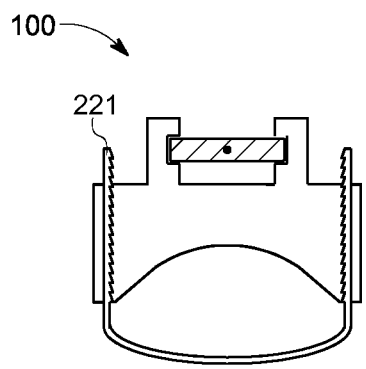
FIG. 2C shows a zip-tie-based guide fastener in accordance with an embodiment.

By way illustration and not limitation, examples of two fasteners are discussed with respect to FIGS. 2B and 2C. FIG. 2B shows a sheath-based fastener whereby the fasteners 102 are attached to a sheath 211 that is configured to slide over an end of a probe 103 and into an operable position. Although the sheath 211 is shown as a closed sheath, in another embodiment, the sheath 211 can be configured as a sleeve that this open-ended to slide over the probe 103. By way of example, the sheath 211 can be made of a flexible material (e.g., rubber) to provide for stretching and tension on probe 103.

In another embodiment, as shown in FIG. 2C, the guide 100 can be configured with a zip-tie style fastener in place of a lower mount mechanism to secure the guide 100 to the probe 100. In other embodiments (now shown), the guide 100 may be configured to fit to the probe 100 using screws, flanges, or other temporary, permanent, or semi-permanent fastening systems. In addition, although the fasteners 102 of the guide 100 may be configured as generic and adjustable fasteners that can support probes of a variety sizes and shapes, it is also contemplated that the fasteners can be fit to specific models of probes for customized applications.

Figure 3:
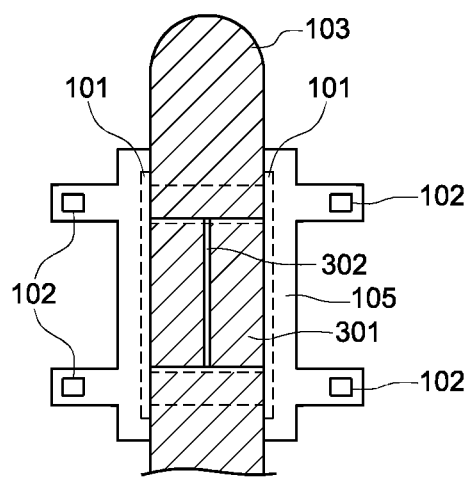
FIG. 3 shows a top view of a guide secured to a probe in accordance with an embodiment.

FIG. 3 is a top view of a guide secured to a probe. This figure includes a sliding platform 301, a drilled hole 302, stabilization bars 101, fasteners 102, an upper mount 105, and a probe 103. As previously described, in one embodiment, the drilled hole 102 can accommodate or support various sizes and/or configurations of needles (e.g., straight needles, curved needles, etc.) and instruments for performing a biopsy so that the needle can be aligned relative to the probe 103, thereby, also providing an alignment between the needle and an image produced by the ultrasound probe 103. In one embodiment, the drilled hole 102 can support an access needle through which a biopsy needle or other instrument can be introduced at a known alignment with respect to the probe 103. In addition, although the hole 102 to support, e.g., an access needle or other instrument is showed in a central midline position, the location of the hole can be configured at any position of the guide 100.

Figure 4:
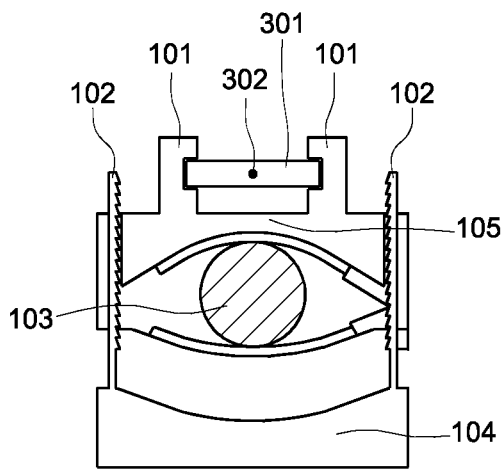
FIG. 4 shows a cross-sectional view of the back of a guide secured to a probe in accordance with an embodiment.

FIG. 4 is a cross-section view of the back of a guide secured to a probe including a sliding platform 301, drilled hole 302, stabilization bars 101, lower mount 104, upper mount 105, fasteners 102, and probe 103.

Figure 5:
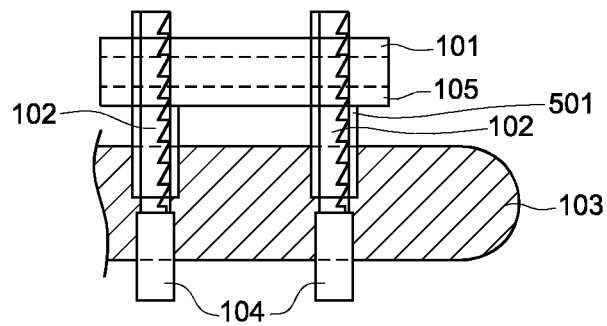
FIG. 5 shows a magnified view of a guide secured to a probe in accordance with an embodiment.

FIG. 5 is a magnified view of FIG. 1. FIG. 5 demonstrates minimum dimensions of preferred embodiments, which includes stabilization bars 101 and upper mount 105 from 30 mm to 50 mm long; the upper mount 105 with a height ranging from 10 mm to 15 mm; the stabilization bars 101 with a height that is about ⅓ of the height of the upper mount 105; fasteners 102 with a height of about 25 mm and 10 mm wide; a lower mount 104 10 mm wide. Additionally, the off-set 501 from the distal point of the stabilization bar 105 to the fasteners 102 may be 5 mm. It is contemplated that any of these dimensions may vary, including the stabilization bar 101, which may be longer than the upper mount 105.

Figure 6:
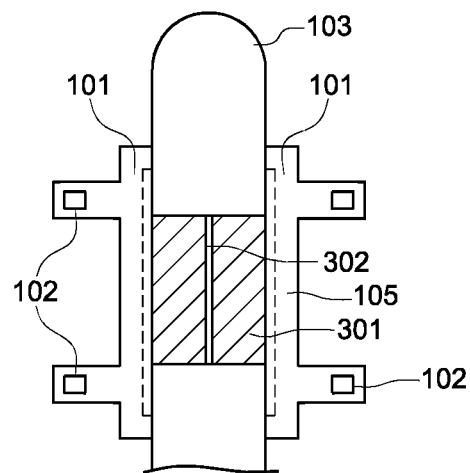
FIG. 6 is a magnified top view of a guide fastener in accordance with an embodiment.

FIG. 6 is a magnified internal view of the guide fastener shown in FIG. 2. FIG. 6 demonstrates minimum dimensions of preferred embodiments. The fasteners 102 may have an aperture 201 to accommodate teeth 202, wherein the fastener 102 is 5 mm to 10 mm wide. Additionally, the sliding platform 301, which may be from 12 mm to 25 mm wide, is slightly shorter than the distance between the two stabilization bars 101 as to accommodate the sliding platform while also securing it to the guide 100.

Figure 7:
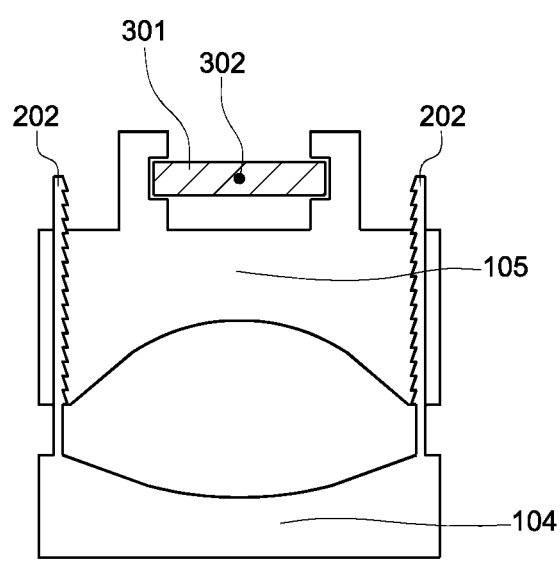
FIG. 7 is a magnified view of a guide in accordance with an embodiment.

FIG. 7 is a magnified view of the guide depicted FIG. 3, without the probe 103. FIG. 7 also demonstrates minimum dimensions of preferred embodiments, wherein the height of the upper mount 105 ranges from 5 mm to 10 mm; and the teeth 202 is from 5 mm to 8 mm wide.

Figure 8:
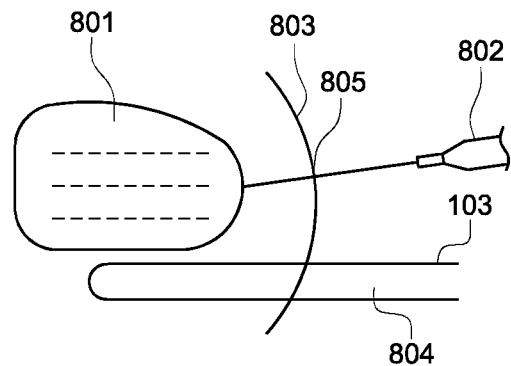
FIG. 8 is a side view of a biopsy instrument that has penetrated the prostate in accordance with an embodiment.

FIG. 8 is a side view of a biopsy instrument that is about to penetrate the prostate, including a prostate 801, a probe 103, a biopsy instrument 802, a perineum skin 803, an anus 804, and a perforation point 805. The probe 103 is inserted into the anus 804 to provide real-time images of the biopsy, including images of the biopsy instrument 802 and the prostate 801. It is contemplated that the biopsy instrument 802 includes a needle and any other instrument capable of performing a biopsy.

Figure 9:
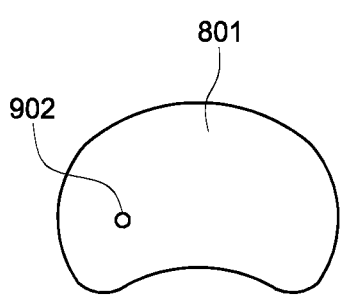
FIG. 9 is a front view of a designated area of the prostate where a biopsy instrument will penetrate in accordance with an embodiment.
Figure 10:
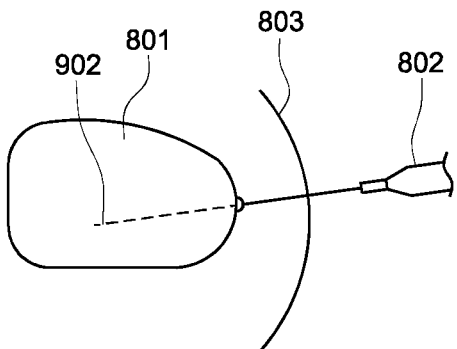
FIG. 10 is a side view of a biopsy instrument penetrating the prostate in accordance with an embodiment.

FIG. 9 is a front view of a targeted area 902 of the prostate 801. FIG. 10 is a side view of a biopsy instrument penetrating the prostate 801, including a targeted area 902 of the prostate 801. The targeted area 902 is reached by biopsy instrument 802 after perforating perineum skin 803.

Figure 11:
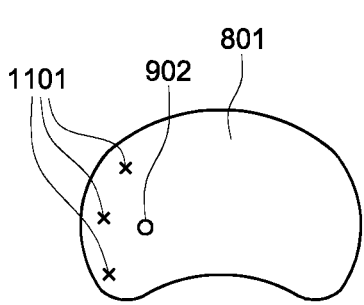
FIG. 11 is a front view of a designated area of the prostate where a biopsy instrument will penetrate with areas in which the cell or tissue specimen has already been extracted in accordance with an embodiment.

FIG. 11 is a front view of a targeted area of the prostate where a biopsy instrument will penetrate with areas in which the cell or tissue specimen has already been extracted. FIG. 11 depicts both an extracted area 1101 and a targeted area 902. The possibility of viewing the area in which the cell or tissue specimen has already been extracted permits the practitioner to avoid placing the access needle in an area that cell or tissue specimen has already been extracted. This allows the biopsy to be more efficient and more accurate.

Figure 12:
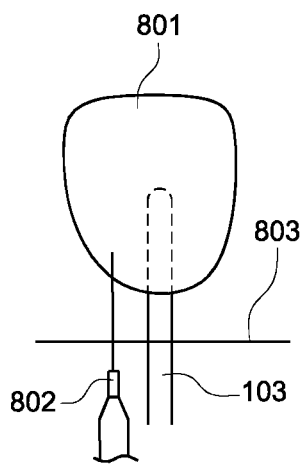
FIG. 12 is a top view of a biopsy instrument that has penetrated the prostate in accordance with an embodiment.
Figure 13:
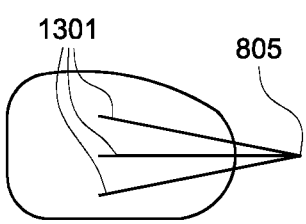
FIG. 13 is a side view of a prostate and the path of the biopsy instrument.

FIG. 12 is a top view of FIG. 8, depicting a prostate 801, perineum skin 803, a probe 103, and a biopsy instrument 802. FIG. 13 is a right side view of a prostate and the path of the biopsy instrument including the path of the biopsy instrument 1301 and the perforation point 805. FIG. 13 illustrates that only one initial perforation to the skin of the patient is necessary in order to extract one or more cell or tissue specimens.

Figure 14:
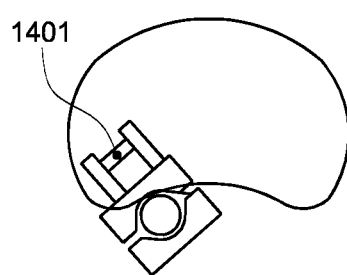
FIG. 14 is a front view of a guide positioned at a designated area of the prostate in accordance with an embodiment.
Figure 16:
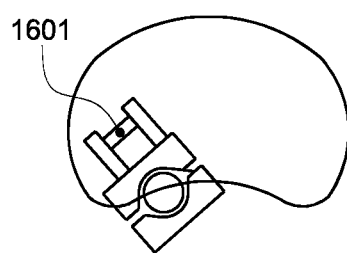
FIG. 16 is a front view of a guide positioned at another designated area of the prostate in accordance with an embodiment.
Figure 18:
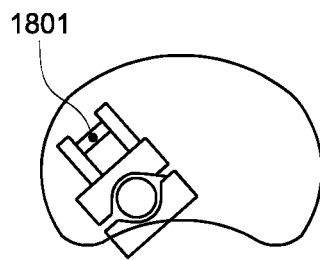
FIG. 18 is a front view of a guide positioned at a higher designated area of the prostate, according to one embodiment.

FIG. 14 is a front view of a guide determining a lower targeted or suspicious area 1401 of the prostate in which to penetrate the biopsy instrument, a prostate, and a probe. FIG. 16 is a front view of a guide determining a mid target or suspicious area 1601 of the prostate in which to penetrate the biopsy instrument, a prostate, and a probe. FIG. 18 is a front view of a guide determining a higher targeted or suspicious area 1801 of the prostate in which to penetrate the biopsy instrument, a prostate, a probe. FIGS. 14, 16, and 18 demonstrates the variety of angles and positions in which a guide may be positioned in order to reach several regions of the prostate, such as the lateral region, mid region, and apical region. In order to the able to reach these areas, FIGS. 14, 16, and 18 demonstrate how the upper mount 105, the stabilization bars 101, or a combination of thereof can adjust in order to reach a lower targeted or suspicious area 1401, a mid targeted or suspicious area 1601, or a higher targeted or suspicious area 1801 of the prostate.

Figure 15:
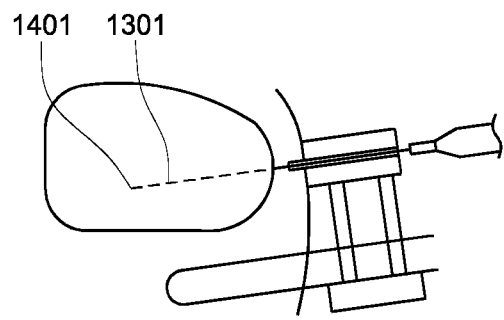
FIG. 15 is a side view of a guide positioned at a designated area of the prostate in accordance with an embodiment.
Figure 17:
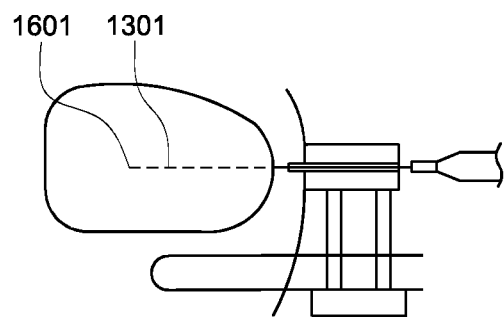
FIG. 17 is a side view of a guide positioned at another designated area of the prostate.
Figure 19:
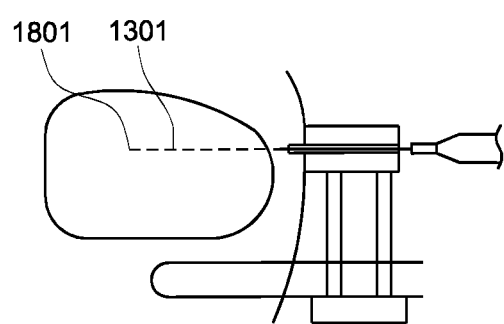
FIG. 19 is a right side view of a guide positioned at a higher designated area of the prostate in comparison with that shown in FIGS. 14-17 in accordance with an embodiment.

FIGS. 15, 17, and 19 demonstrate a side view of FIGS. 14, 16, and 18 and the paths of the biopsy instrument 1301 taken by a biopsy instrument to reach lower targeted or suspicious area 1401, a mid targeted or suspicious area 1601, or a higher targeted or suspicious area 1801 of the prostate.

Figure 20:
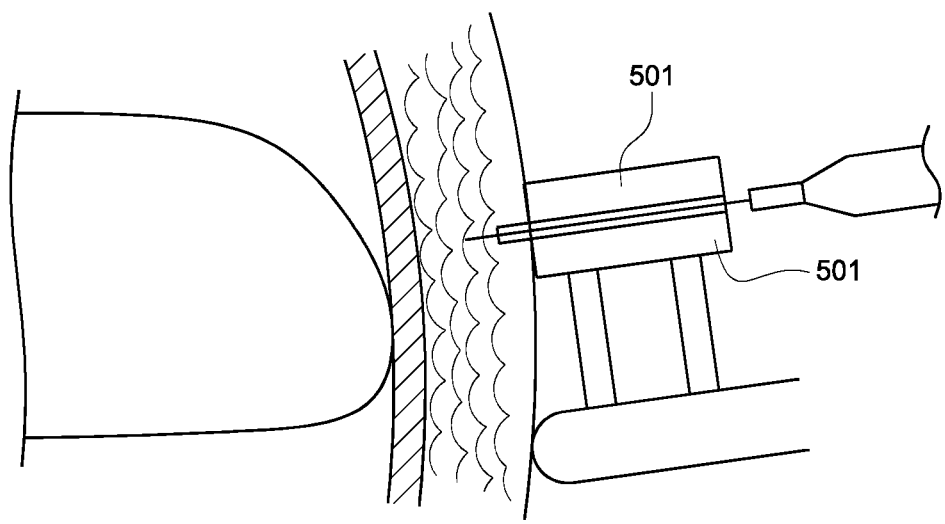
FIG. 20 is a side view of a guide and a biopsy instrument firmly penetrating a fat plane and perineum skin of a patient in accordance with an embodiment.

FIG. 20 is a right side view of a guide, and a biopsy instrument firmly penetrating a fat plane of perineum skin, including offset 501 of a stabilization bar 101. This allows for stabilization in a patient with an excessive amount of perineal subcutaneous tissue, fat, or a combination thereof. A larger stabilization bar 101 will assist in locking the guide in the proper ultrasound plane. Accordingly, the offset 501 may longer than 5 mm for these purposes.

Figure 21:
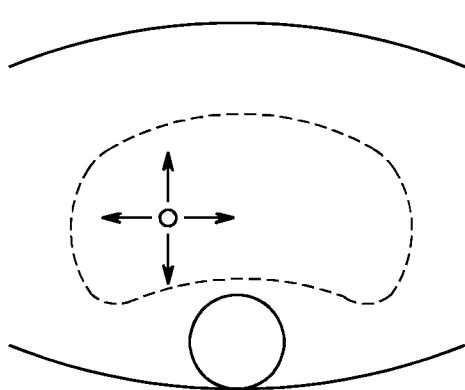
FIG. 21 is a view of an access needle positioned at the access site in accordance with an embodiment.

FIG. 21 is a front view of a prostate, a probe, a targeted or suspicious area, wherein the biopsy instrument may reach any area of the prostate. FIG. 21 demonstrates that the biopsy instrument can reach the entire prostate while using only one perforation point 805. After obtaining one cell or tissue specimen, the biopsy instrument 802 may be partially retrieved from the perineum area at a point in which the distal point of the biopsy instrument 802 is redirected to another targeted or suspicious area. Then, the biopsy instrument (usually the needle of the biopsy instrument) is inserted to the second targeted or suspicious area for obtaining a cell or tissue specimen of another area of the prostate.

Figure 22:
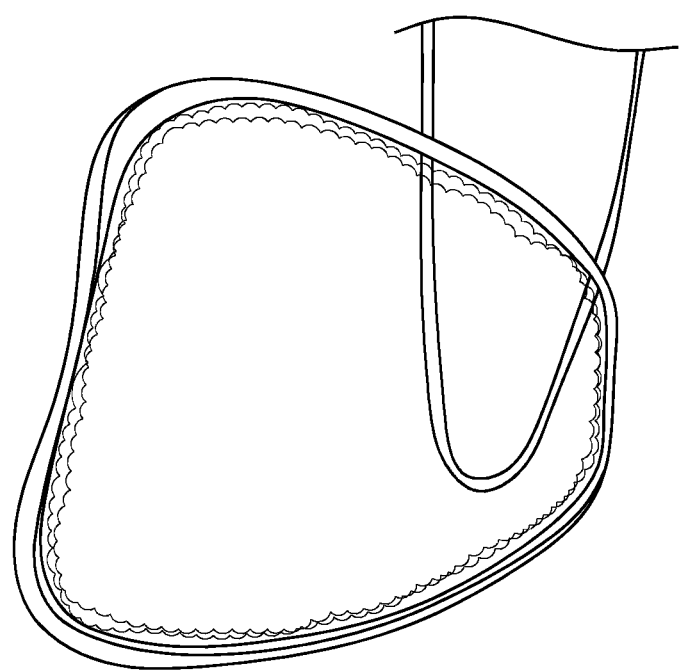
FIG. 22 is a magnified view of the right side of a prostate and a biopsy instrument in accordance with an embodiment.

FIG. 22 is a magnified view of the right side of a prostate and a biopsy instrument. FIG. 22 depicts the location of the biopsy instrument inside the prostate and the other paths in which the biopsy instrument may take utilize for additional samples or retrieval. In embodiments, the biopsy needle or other instruments do not reach the initial part of the penis, which is in a different plane from the prostate.

Figure 23:
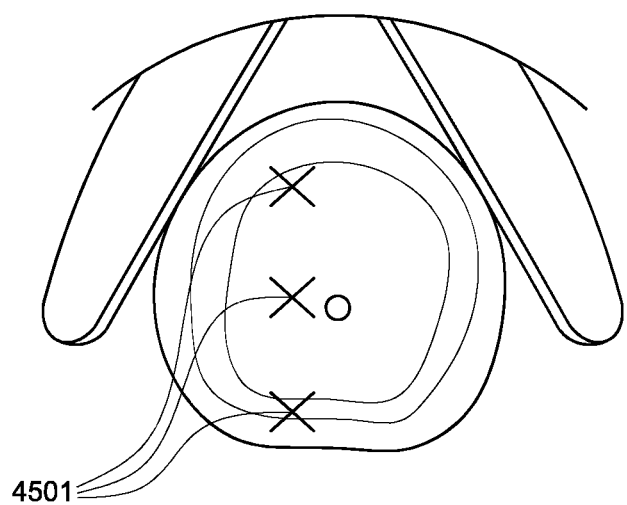
FIG. 23 is an image of the front side of a prostate and a biopsy instrument being retrieved from the prostate, and other targeted areas in accordance with an embodiment.

FIG. 23 is an image of the front side of a prostate and a biopsy instrument being retrieved from the prostate, and other targeted areas. FIG. 23 shows a procedure being applied to the apical region of the prostate.

The urethra should be avoided in any part of the procedure, but it is mostly important when extracting cell or tissue specimens from the apical region of the prostate, when the chances of perforation is greater. After several extractions, the practitioner is able to see the blood streak from where the cell or tissue specimen was taken so as to avoid overlapping.

After this procedure, the patient may be put with restriction for no more than 1 day. If the patient is put on restriction for 1 day, after the one-day-restriction, no restriction is made.

Figure 24:
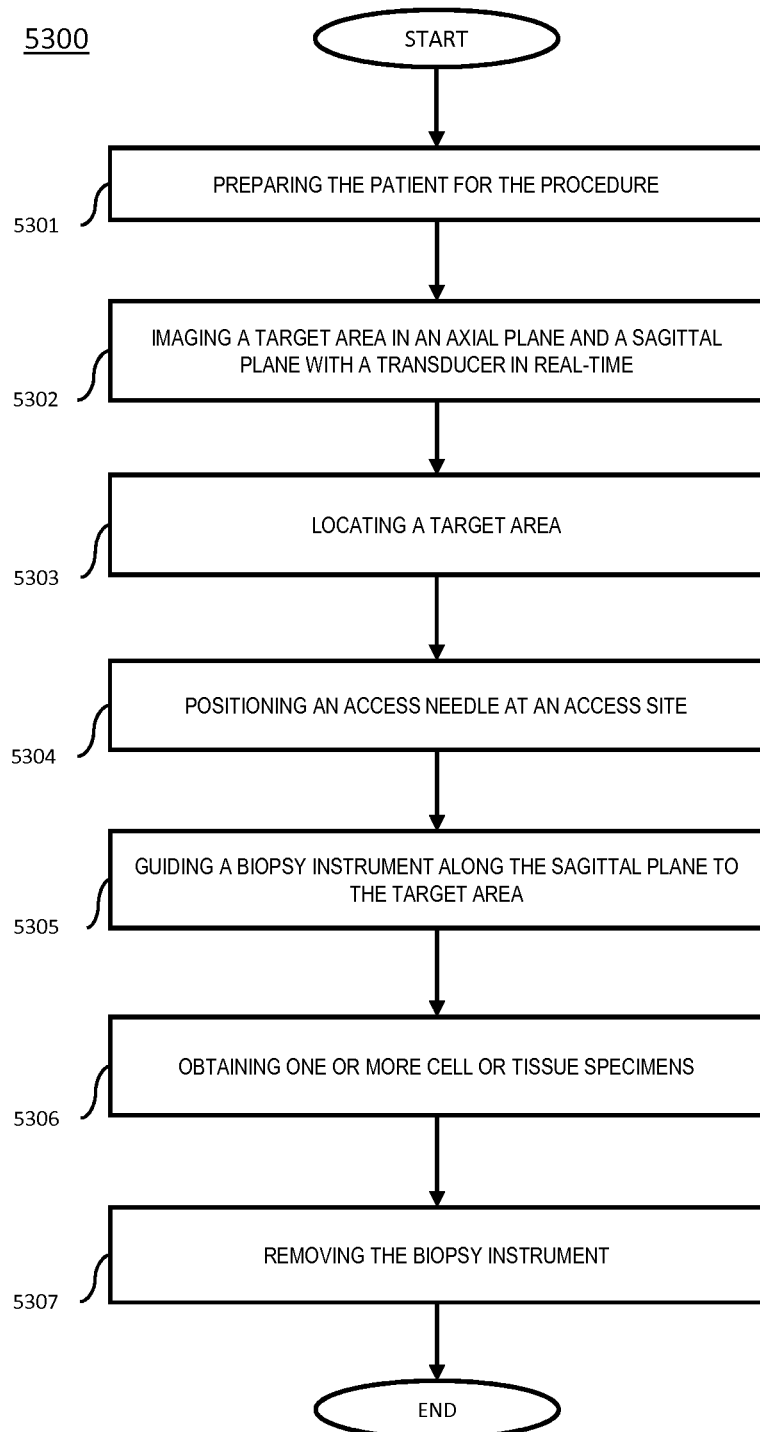
FIG. 24 shows a method for performing a prostate biopsy in accordance with an embodiment.

In an embodiment, the biopsy system performs the processes 2400 of FIG. 24. At 2401, a patient is prepared for the biopsy procedure by having the patient get into a lithotomic position, prone position, or any position that allows for access to the perineal area. The biopsy procedure may be a prostate biopsy. In some embodiments, the patient's scrotum is elevated using, for example, two strips of plastic tape. The perineum is prepared with an antiseptic solution to the perineal area, for example, the antiseptic solution may include betadine.

At 2402, a target area or object, such as the prostate, is imaged. Imaging may be performed with a transducer, such as an ultrasound probe. Imaging of a target area may be in a sagittal and/or axial plane and may be performed in real-time with direct visualization. Utilizing the real-time image, a user can identify areas of interest, e.g. suspicious areas or the target area or object at 2403.

The user may determine an access site for positioning an access needle. At 2404, an access needle is positioned at an access site in subcutaneous tissue of the perineum. The access site may be at a midpoint between a lateral edge of the prostate and the urethra along an x axis, and a midpoint between an anterior capsule and a posterior capsule along a y axis. The access needle is guided and positioned at the access site by using the guide.

At 2405, a biopsy instrument is guided to the target or suspicious areas or object. The biopsy instrument may include a biopsy needle. The guiding of the biopsy instrument can be facilitated by using the real-time visualization provided by the transducer. Real-time visualization also facilitates obtaining tissue or cell specimens from an accurate point in the prostate, for example. The method allows for one or more tissue or cell specimens to be obtained from a bodily organ, such as the prostate at 2406, and permits access to the prostate from different angles through a single initial access needle.

At 2407, the biopsy instrument may be retrieved and removed from the patient. The method may include calculating the volume of the prostate by positioning the access needle at a mid point in x axis from the lateral edge of the prostate to the urethra.

Figure 25:
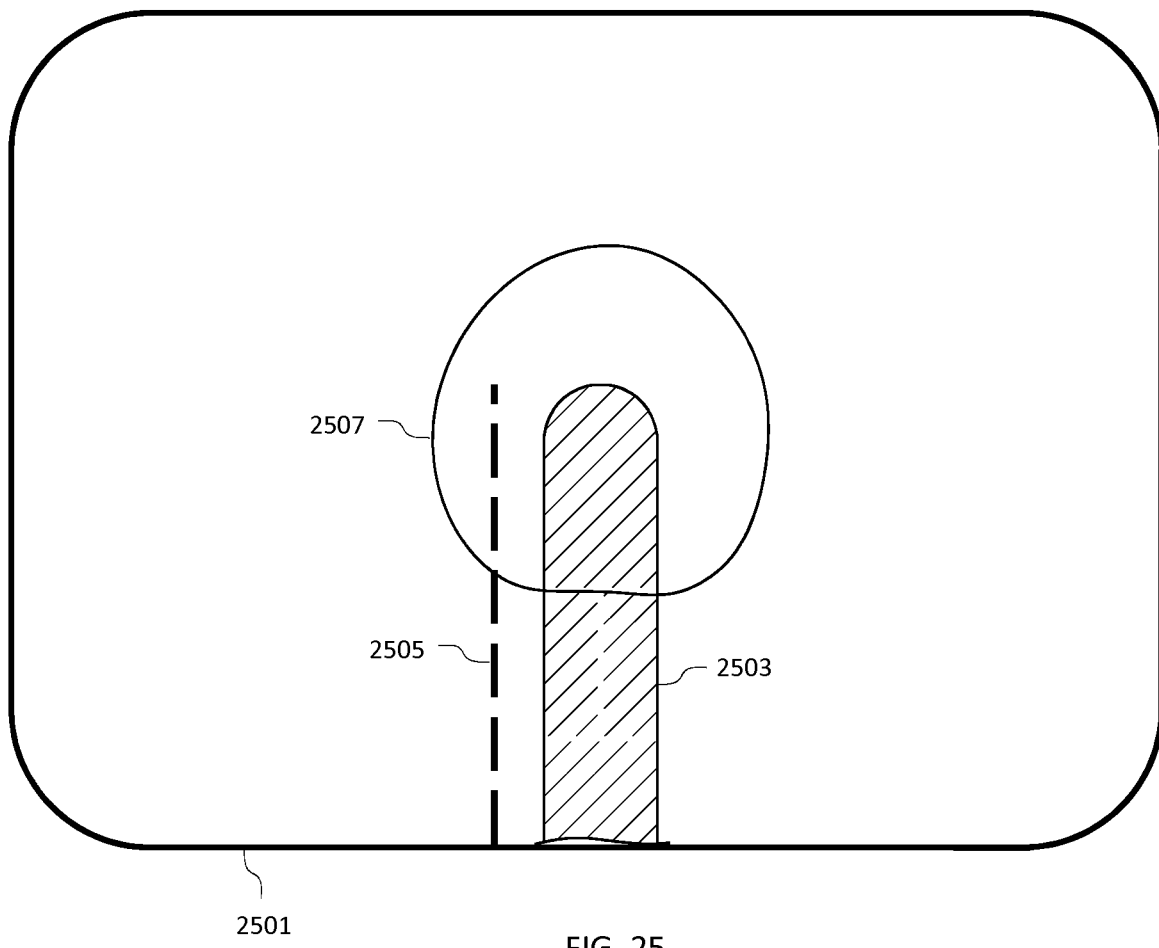
FIG. 25 is an ultrasound image showing a transducer, access needle path extending from an access point at a perineal site to a prostate, and a prostate.

FIG. 25 shows an ultrasound 2501 showing a transrectal probe 2503 and an access needle guide line 2505. The needle guide line enables the practitioner to observe a needle path whereby the access needle has contacted the prostate 2507, thereby enabling the practitioner to avoid overlapping sampling, and to avoid perforating the prostate.

Figure 26A:
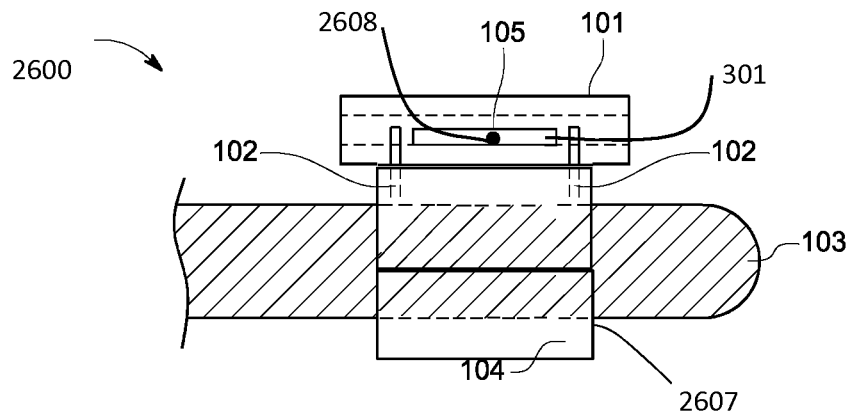
FIGS. 26A-26C show side views of a guide configured with a pivoting mount in accordance with an embodiment.
Figure 26B:
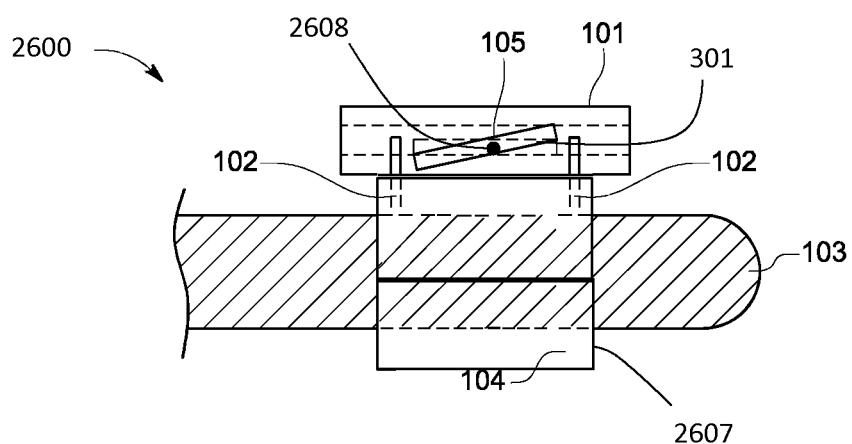
Figure 26C:
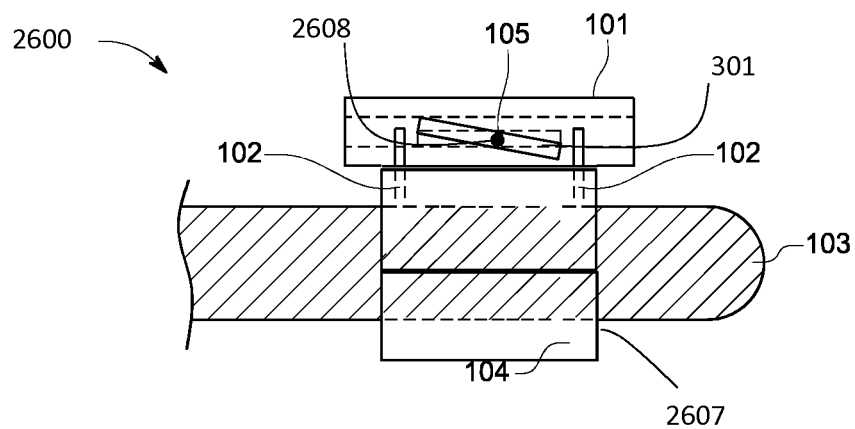

FIGS. 26A-26C show side views of an alternative embodiment of a guide 2600 secured to a probe including a stabilization bar 101, fasteners 102, probe 103, lower mount 104, and an upper mount 105. The stabilization bar 101 is an extension of the upper mount 105, as further discussed in FIG. 4. In embodiments, the distance between the fasteners 102 and the upper mount 105 may be adjustable to accommodate various applications and body habitus.

The guide 2600 includes a sliding platform 301. The guide is fitted to the probe 103 by a sleeve 2607. The sleeve 2607 is formed by the lower mount 104 and the upper mount 105. The sleeve 2607 may be configured to slide over an end of the probe 103 into an operable position as shown in FIGS. 26A-26C. The sleeve 2607 is a partial sleeve that has an opening at both ends of the sleeve 2607 to enable slidable mounting to and removal from the probe 103.

The sliding platform 301 of the guide 2600 may be pivotably mounted to enable movement in a direction perpendicular to a longitudinal axis of the probe 103, as shown in FIGS. 26A-26C. In particular FIGS. 26A-26C show that the sliding platform 103 is fixed to the guide at a pivot point 2608. The sliding platform 103 is configured to pivot at pivot point 2608 to enable, for example, normal or vertical adjustment of an access needle (not shown) in directions perpendicular to a longitudinal axis of the probe 103 while ensuring that a longitudinal axis of the access needle (not shown) remains parallel to the longitudinal axis of the probe 103.

For example, FIG. 26A shows a sliding platform 301 in a first position at which a lateral planar surface of the platform 301 extends in a direction parallel to the longitudinal axis of the probe 103. FIG. 26B shows the sliding platform 301 pivoted to a second position wherein a front end the platform 301 is disposed a distance from the probe 103 that is greater than a distance between an opposite rear portion of the platform 301 and the probe 103. FIG. 26C shows the sliding platform 301 pivoted to a third position wherein the rear end of the platform 301 is disposed a distance from the probe 103 that is greater than a distance between the opposite front end of the platform 301 and the probe 103.

In another embodiment, the method may be performed without the patient taking antibiotics or undergoing bowel preparation before having the procedure. During the procedure, the practitioner may administer an anesthetic to the patient, for example, lidocaine, or any type of local, anesthetic. The lidocaine may be included in a solution having 1% of lidocaine.

In an embodiment, the suspicious area is located by using a transducer. The transducer may be any type of transrectal robe for prostate cancer, such as an ultrasound probe, or any type of transducer capable of imaging the prostate and the extraction device. The biopsy may be performed using a biopsy gun, a suction-mechanism, or any type of instrument that is small enough to be introduced through the access needle and capable of extracting the tissue or cell specimen. The biopsy may be performed while the patient is in a lithotomy position, prone position, or any position that allows for access to the perineal area.

In another embodiment, methods may include applying an antiseptic solution to the perineal area such as betadine, or any other substance that reduces the possibility of infection, sepsis, or putrefaction.

In another embodiment, the ultrasound probe may be a B&K 8848 transrectal ultrasound probe, or any other ultrasound capable of causing visualization of the prostate and the extraction device. The frequency range may be 5-12 MHZ, and the focal range may be 3-60 mm. The ultrasound probe may be able to cause the visualization of the prostate and extraction devices at least in the axial plane, sagittal plane, or a combination thereof.

In another embodiment, methods may include attaching a needle to a luer lock syringe, which may contain an anesthetic, or any other type of device capable of retaining its contents and to dispense its contents through the needle. A biopsy gun or any other instrument may be attached to the needle for inserting or extracting any substance through the lumen of the access needle.

In another embodiment, the method includes releasing the syringe from the needle after the anesthetic is injected. The method may include dividing the prostate in three different regions and designating lateral, mid, apical prostate, and may include labeling the tissue or cell specimen containers, which will identify the tissue or cell specimens.

In another embodiment, a biopsy gun may be an 18 gauge biopsy gun, or any other size that is capable of being coaxially inserted thru the lumen of the access needle.

In another embodiment, methods may include securing the guide to the probe. This will permit the practitioner to take the biopsy gun as many times as necessary using his or her other hand, and, consequently, extract multiple tissue or cell specimens. It is contemplated that this can be done without assistance of any other person, and that the biopsy gun may also be attached to the guide in order to permit the surgeon to e.g. label the container with the tissue or cell specimen while performing the biopsy. The method may also include monitoring all the actions in the prostate thru a display device, which will transmit images captured by the probe.

In another embodiment, methods may include moving the needle in x, y, and z planes. By being able to move the need in x, y, and z planes, the surgeon is capable of extracting tissue or cell specimens from several different areas of the prostate without having to retrieve the needle and preventing other perforation of the patient's skin.

Methods may further include removing the access needle from the perennial area. Removal of the access needle may be performed while the biopsy gun is secured to the access needle or after the biopsy gun has been detached from the access needle.

Methods may include realigning the needle in the desired prostate region. If the surgeon wishes to start at the right lateral prostate region and notices that the needle tip is not directed at the lateral region, the surgeon rolls the ultrasound probe slightly and to note that the needle tip is directed to the desired region, then the surgeon may realign the needle to obtain tissue or cell specimen. The surgeon may realign the needle using one hand while having the needle attached to the biopsy gun, which may be attached to the probe through the guide.

Methods may include identifying the area in which a biopsy has already been performed. After each extraction of tissue or cell specimen during the biopsy, a hyperechoic streak remains visible on ultrasound display. This allows the surgeon to identify the area of the prostate and that an extraction has been made, as to allow the surgeon to prevent overlap of extractions.

In another embodiment, methods may include identifying the path of the urethra. This allows the surgeon from preventing passing the biopsy needle thru or into this path. In another embodiment, the method includes pressuring the perineum. In yet another embodiment, the method includes applying bacitracin to the skin at the puncture site or any other type of topical preparation for preventing the possibility of infection. In another embodiment, positioning the access needle is performed without the need of a biopsy grip, wherein the guide provides the precise point for the biopsy.

An apparatus and system in accordance with embodiments discussed above is used to carry out these methods. In an alternative embodiment of apparatus and systems, a guide may not include a lower mount, and may include an access needle. The guide includes a stabilization bar, sliding platform, a hole located in approximately the center of the platform, an upper mount, teeth, aperture, arms, and a connector. The access needle includes a hub and is secured to the guide. The teeth may be part of, or may be attached to, a lower mount. The teeth may be inserted into the aperture in order to secure the guide to a probe, for example. It is contemplated that the combination of the aperture and the teeth may form a fastener mechanism. In embodiments, connector is part of, or may be attached to, an access needle, and may be secured to the upper mount in order to provide stabilization of the access needle and to allow the practitioner to move the access needle by merely moving, for example, a probe that may be secured to the guide.

A connector and a hub permit the use of various other instruments such as, for example, a non-biopsy instrument, to be secured. A biopsy instrument may be inserted into the access needle in order to reach a targeted area. The upper mount may include arms. In embodiments, the arms may be shorter, longer, or may not exists, in which case the aperture is disposed directly in the upper mount. When the aperture is directly in the upper mount, upper mount may be longer, thicker, or a combination thereof.

In some embodiments, the guide may include lower mounts that have teeth. Arms may extend from the upper mount to allow the height of the guide to be adjusted and to be placed farther from or closer to the probe. The arms permit the access needle to be maintained at a certain distance from a probe. In embodiments, the material of the guide may be a plastic or any other material, including other plastic materials, or any other material that is cost effective. In embodiments, the guide may be reusable and may be formed with a stainless steel. The lower mount may be curvilinear and flexible to allow the lower mount to bend if necessary to secure the guide to the probe.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed:

1. A method of performing a transperineal prostate biopsy procedure on a prostate of a patient using an ultrasound probe, the method comprising:
   positioning a pair of stabilization members of a biopsy guide proximate of a perineal access site leading to the prostate, the pair of stabilization members spaced apart from each other and supporting a platform configured to slide along a portion of a length of the pair of stabilization members, the platform configured to support an access needle, the biopsy guide secured to the ultrasound probe such that the platform and the access needle are configured to move relative to the pair of stabilization members and the ultrasound probe;
   supporting the access needle to the platform; and
   sliding the platform and access needle relative to the pair of stabilization members and the ultrasound probe so the access needle extends into the perineal access site.

2. The method of claim 1, further comprising inserting a biopsy needle through the access needle and into a first location within the prostate.

3. The method of claim 2, further comprising inserting the biopsy needle through the access needle and into a second location within the prostate, the second location being different than the first location.

4. The method of claim 3, wherein the access needle remains positioned within the perineal access site during the insertion of the biopsy needle into both of the first and second locations.

5. The method of claim 1, wherein positioning the pair of stabilization members of a biopsy guide proximate of the perineal access site comprises contacting a distal end of the pair of stabilization members with a perineal skin of the patient.

6. The method of claim 1, wherein sliding the platform and access needle relative to the pair of stabilization members and the ultrasound probe so the access needle extends into the perineal access site is performed under ultrasound guidance via the ultrasound probe.

7. The method of claim 1, wherein the platform comprises a hole extending there though, and wherein supporting the access needle to the platform comprises extending a shaft of the access needle through the hole of the platform.

8. The method of claim 7, wherein the hole is centrally positioned on the platform.

9. The method of claim 1, wherein a grooved arrangement between the platform and the pair of stabilization members permits the platform to slide relative to the pair of stabilization members.

10. The method of claim 9, wherein the pair of stabilization members includes grooves, and the platform includes outer portions configured to slide within the grooves.

11. The method of claim 1, wherein the platform and the pair of stabilization members are part of an upper mount of the biopsy guide, the biopsy guide further comprising a lower mount configured to couple to the upper mount, and configured to engage the ultrasound probe so as to secure the upper mount relative to the ultrasound probe.

12. The method of claim 1, wherein the length of the pair of stabilization members is generally parallel to a longitudinal axis of the ultrasound probe when the biopsy guide is secured to the ultrasound probe.

13. A method of performing a transperineal prostate biopsy procedure on a prostate of a patient using an ultrasound probe, the method comprising:
   inserting an access needle into a perineal access site leading to the prostate, the access needle engaged with a platform that is configured to slide on a pair of stabilization members of a biopsy guide, the access needle being centrally positioned between the pair of stabilization members when the access needle is engaged with the platform; and
   inserting a biopsy needle through the access needle and into a first location within the prostate.

14. The method of claim 13, further comprising inserting the biopsy needle through the access needle and into a second location within the prostate, the second location being different than the first location.

15. The method of claim 14, wherein the access needle remains positioned within the perineal access site of the prostate during the insertion of the biopsy needle into both of the first and second locations within the prostate.

16. The method of claim 13, further comprising contacting a distal end of the pair of stabilization members against a perineal skin of the patient prior to inserting the access needle into the perineal access site.

17. The method of claim 16, further comprising positioning the perineal skin with the distal end of the pair of stabilization members so as to orient the access needle for insertion of the biopsy needle.

18. The method of claim 13, wherein inserting the access needle into the perineal access site comprises sliding the access needle and platform along a portion of a length of the pair of stabilization members.

19. The method of claim 18, further comprising securing the platform at a distal position along the length of the pair of stabilization members.

20. The method of claim 13, further comprising obtaining at least one of a cell and tissue sample from the prostate with the biopsy needle.

21. The method of claim 1, further comprising:
   inserting a needle through the access needle and into tissue of the patient; and
   injecting a substance into the tissue.

22. The method of claim 21, wherein the tissue is outside the prostate.

23. The method of claim 21, wherein the substance comprises an anesthetic.

24. The method of claim 13, further comprising:
   inserting a needle through the access needle and into tissue of the patient; and
   injecting a substance into the tissue.

25. The method of claim 24, wherein the tissue is outside the prostate.

26. The method of claim 24, wherein the substance comprises an anesthetic.

27. A method of performing a transperineal prostate biopsy procedure on a prostate of a patient using an ultrasound probe, the patient comprising perineal skin leading to the prostate, the method comprising:
   engaging a pair of stabilization members of a biopsy guide with the perineal skin at a perineal access site of the patient;

inserting an access needle into the perineal skin at the perineal access site in a first trajectory, the access needle positioned between the pair of stabilization members; and taking a first biopsy by inserting a first biopsy needle through the access needle and into a first location within the prostate.

28. The method of claim 27, wherein the access needle is engaged with a platform that is configured to slide on the pair of stabilization members of the biopsy guide.

29. The method of claim 27, further comprising inserting a needle through the access needle and into tissue of the patient; and injecting a substance into the tissue.

30. The method of claim 29, wherein the tissue is outside the prostate.

31. The method of claim 29, wherein the substance comprises an anesthetic.

32. The method of claim 27, further comprising moving the pair of stabilization members of the biopsy guide relative to the prostate and with the access needle still inserted into the perineal skin such that the access needle is oriented in a second trajectory that is different than the first trajectory.

33. The method of claim 32, further comprising taking a second biopsy by inserting a second biopsy needle through the access needle and into a second location within the prostate, the second location being different than the first location.

34. The method of claim 32, wherein the biopsy guide is coupled to the ultrasound probe, and wherein moving the pair of stabilization members of the biopsy guide is facilitated by moving the ultrasound probe.

35. The method of claim 27, wherein the biopsy guide is coupled to the ultrasound probe.

36. A method of performing a transperineal prostate biopsy procedure on a prostate of a patient using an ultrasound probe configured to provide imaging in at least a sagittal plane, the method comprising:

inserting an access needle into a perineal access site leading to the prostate, the access needle engaged with a platform that is configured to slide on a pair of stabilization members of a biopsy guide that is secured to the ultrasound probe, the access needle positioned within the sagittal plane when the access needle is engaged with the platform and when the ultrasound probe provides imaging in the sagittal plane; and inserting a biopsy needle through the access needle and into a first location within the prostate.

37. The method of claim 36, further comprising inserting the biopsy needle through the access needle and into a second location within the prostate, the second location being different than the first location.

38. The method of claim 37, wherein the access needle remains positioned within the perineal access site of the prostate during the insertion of the biopsy needle into both of the first and second locations within the prostate.

39. The method of claim 36, further comprising contacting a distal end of the pair of stabilization members against a perineal skin of the patient prior to inserting the access needle into the perineal access site.

40. The method of claim 36, further comprising obtaining at least one of a cell and tissue sample from the prostate with the biopsy needle.

41. The method of claim 36, further comprising:

inserting a needle through the access needle and into tissue of the patient; and injecting a substance into the tissue.

42. The method of claim 41, wherein the tissue is outside the prostate.

43. The method of claim 41, wherein the substance comprises an anesthetic.

* * * * *

(12) EX PARTE REEXAMINATION CERTIFICATE (12952nd)
United States Patent
Allaway

(10) Number: US 11,096,762 C1
(45) Certificate Issued: *Jun. 27, 2025

(54) METHOD, SYSTEM, AND DEVICE FOR PLANNING AND PERFORMING GUIDED AND FREE-HANDED TRANSPERINEAL PROSTATE BIOPSIES

(71) Applicant: Corbin Clinical Resources, LLC, Cumberland, MD (US)

(72) Inventor: Matthew J. Allaway, Cumberland, MD (US)

(73) Assignee: CORBIN CLINICAL RESOURCES, LLC, Cumberland, MD (US)

Reexamination Request:
No. 90/019,354, Dec. 27, 2023

Reexamination Certificate for:
Patent No.: 11,096,762
Issued: Aug. 24, 2021
Appl. No.: 16/115,180
Filed: Aug. 28, 2018

(*) Notice: This patent is subject to a terminal disclaimer.

Related U.S. Application Data

(63) Continuation of application No. 14/677,286, filed on Apr. 2, 2015, now Pat. No. 10,064,681.

(60) Provisional application No. 61/974,826, filed on Apr. 3, 2014.

(51) Int. Cl.
| | | |
|---|---|---|
| A61B 90/00 | (2016.01) | |
| A61B 8/08 | (2006.01) | |
| A61B 8/12 | (2006.01) | |
| A61B 10/02 | (2006.01) | |
| A61B 10/04 | (2006.01) | |
| A61B 17/34 | (2006.01) | |
| A61B 17/00 | (2006.01) | |
| A61B 18/00 | (2006.01) | |
| A61B 18/02 | (2006.01) | |
| A61B 18/12 | (2006.01) | |

(52) U.S. Cl.
CPC ............ *A61B 90/39* (2016.02); *A61B 8/0841* (2013.01); *A61B 8/12* (2013.01); *A61B 10/0241* (2013.01); *A61B 10/04* (2013.01); *A61B 17/3403* (2013.01); *A61B 2010/045* (2013.01); *A61B 2017/00274* (2013.01); *A61B 2017/00477* (2013.01); *A61B 2017/3413* (2013.01); *A61B 2018/00547* (2013.01); *A61B 18/02* (2013.01); *A61B 18/12* (2013.01)

(58) Field of Classification Search
None
See application file for complete search history.

(56) References Cited

To view the complete listing of prior art documents cited during the proceeding for Reexamination Control Number 90/019,354, please refer to the USPTO's Patent Electronic System.

*Primary Examiner* — Catherine S Williams

(57) ABSTRACT

A system for planning and performing a guided and free-handed transperineal prostate biopsy includes a transrectal ultrasound probe, an access needle configured to perforate a perineal access site of a patient, a biopsy gun, and a guide. The guide includes a sliding platform, stabilization bars, upper and lower mounts, and fasteners. The system and guide apparatus is used for locating a target area using the ultrasound probe, positioning the ultrasound and the access needle at respective designated points, precisely measuring the distance to a designated point, and obtaining specimens from a precise point in the prostate, wherein the method is performed free-handed, and multiple tissue or cell specimens may be obtained from the prostate through an initial access needle.

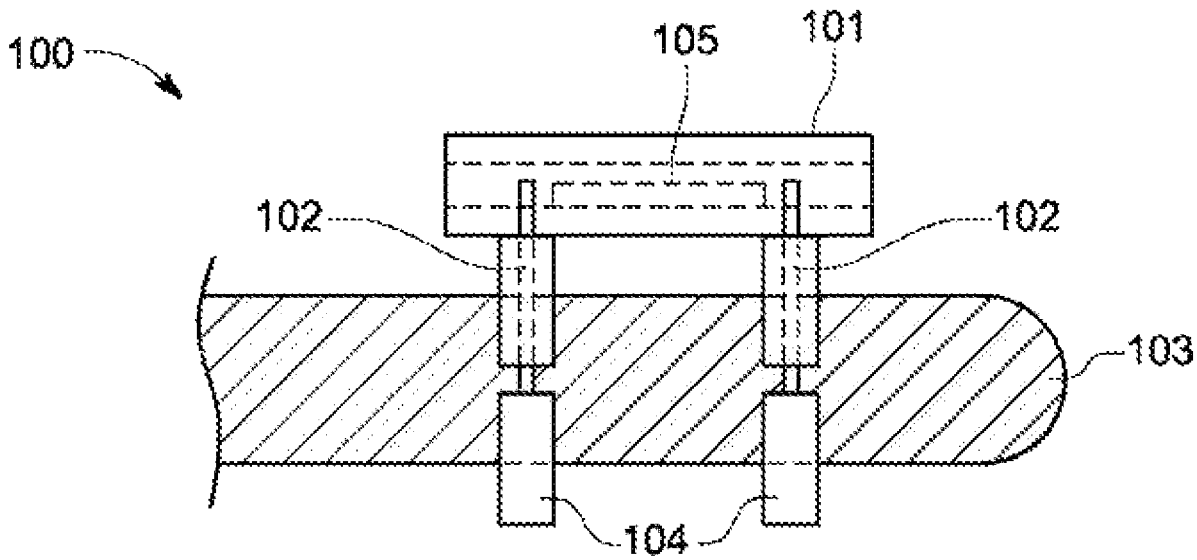

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13-15, 20, 36-38 and 40 is confirmed.

New claims 44-53 are added and determined to be patentable.

Claims 1-12, 16-19, 21-35, 39 and 41-43 were not reexamined.

44. *The method of claim 14, wherein, with the biopsy guide secured to the ultrasound probe, the access needle remains positioned within the perineal access site as the access needle is transitioned from being oriented towards the first location to being oriented towards the second location.*

45. *The method of claim 44, wherein the inserting the biopsy needle through the access needle and into the first location within the prostate occurs along a first path of the access needle, and the inserting the biopsy needle through the access needle and into the second location within the prostate occurs along a second path different from the first path.*

46. *The method of claim 37, wherein the access needle remains positioned within the perineal access site as the access needle is transitioned from being oriented towards the first location to being oriented towards the second location.*

47. *The method of claim 46, wherein the inserting the biopsy needle through the access needle and into the first location within the prostate occurs along a first path of the access needle, and the inserting the biopsy needle through the access needle and into the second location within the prostate occurs along a second path different from the first path.*

48. *The method of claim 13, wherein the access needle is inserted into the perineal access site along a first trajectory leading to the first location within the prostate, the method further comprising, with the biopsy guide secured to the ultrasound probe, moving the ultrasound probe relative to the prostate and with the access needle still inserted into the perineal access site such that the access needle is oriented in a second trajectory that is different from the first trajectory.*

49. *The method of claim 48, further comprising: inserting the biopsy needle or another biopsy needle through the access needle, along the second trajectory, and into a second location within the prostate; and taking a biopsy of the prostate at the second location.*

50. *The method of claim 36, wherein the access needle is inserted into the perineal access site along a first trajectory leading to the first location within the prostate,*

*the method further comprising moving the ultrasound probe relative to the prostate and with the access needle still inserted into the perineal access site such that the access needle is oriented in a second trajectory that is different from the first trajectory.*

51. *The method of claim 50, further comprising: inserting the biopsy needle or another biopsy needle through the access needle, along the second trajectory, and into a second location within the prostate; and taking a biopsy of the prostate at the second location.*

52. *The method of claim 13, further comprising:*

*taking a first biopsy of the first location within the prostate;*

*with the access needle still inserted into the perineal access site and with the biopsy guide secured to the ultrasound probe, adjusting an angle of the access needle by angling the ultrasound probe; and*

*inserting the biopsy needle through the access needle and taking a second biopsy of a second location within the prostate, the first location being different than the second location.*

53. *The method of claim 36, further comprising:*

*taking a first biopsy of the first location within the prostate;*

*with the access needle still inserted into the perineal access site, adjusting an angle of the access needle by angling the ultrasound probe; and*

*inserting the biopsy needle through the access needle and taking a second biopsy of a second location within the prostate, the first location being different than the second location.*

\* \* \* \* \*